(12) United States Patent
Teitelbaum (10) Patent No.: US 6,692,459 B2
(45) Date of Patent: Feb. 17, 2004

(54) ANTI-OCCLUSION CATHETER

(76) Inventor: George P. Teitelbaum, 325 16th St., Santa Monica, CA (US) 90402-2217

( * ) Notice: Subject to any disclaimer, the term of this patent is extended or adjusted under 35 U.S.C. 154(b) by 148 days.

(21) Appl. No.: 09/880,310

(22) Filed: Jun. 13, 2001

(65) Prior Publication Data

US 2002/0010442 A1 Jan. 24, 2002

Related U.S. Application Data

(60) Provisional application No. 60/219,041, filed on Jul. 18, 2000.

(51) Int. Cl.[7] .............................................. A61M 29/00
(52) U.S. Cl. ................ 604/99.02; 604/288.01
(58) Field of Search ............................ 604/19, 27, 28, 604/30, 35, 48, 93.01, 96.01, 99.01–99.02, 99.04, 10.01, 246, 256, 257, 264, 523, 536, 537, 500; 601/288.01

(56) References Cited

U.S. PATENT DOCUMENTS

| | | | |
|---|---|---|---|
| 2,819,718 A | 1/1958 | Goldman | 128/350 |
| 2,919,697 A | 1/1960 | Kim | 128/349 |
| 3,954,102 A | 5/1976 | Buuck | 128/79 |
| 4,566,446 A | 1/1986 | Fogarty | 128/79 |
| 4,890,866 A | 1/1990 | Arp | 285/243 |
| 5,360,403 A | 11/1994 | Mische | 604/101 |
| 5,527,278 A | 6/1996 | Ensminger et al. | 604/93 |
| 5,851,176 A | 12/1998 | Willard | 600/40 |
| 5,928,181 A * | 7/1999 | Coleman et al. | 604/8 |
| 6,045,531 A * | 4/2000 | Davis | 604/101.05 |
| 6,234,995 B1 | 5/2001 | Peacock, III | 604/96.01 |

* cited by examiner

Primary Examiner—LoAn H. Thanh
(74) Attorney, Agent, or Firm—David A. Farah; Sheldon & Mak PC (57) ABSTRACT

A catheter for the administration of fluid or pharmaceutical agents, or for hemodialysis comprising a proximal control end comprising a housing with a proximal end and a distal end, a distal delivery end, an elongated intermediate portion between the proximal control end and a distal delivery end, one or more than one delivery lumen within the intermediate portion extending from the proximal control end to the distal delivery end; one or more than one inflation balloon in each delivery lumen, and one or more than one inflation lumen in the intermediate portion extending from the proximal control end to the one or more than one inflation balloon in the one or more than one delivery lumen, and connected to the one or more than one inflation balloon through one or more than one fenestration, where the proximal control end further comprises a mechanism for aspiration and injection of fluids through the distal delivery end, and where the proximal control end further comprises a mechanism for controlling inflation of the one or more than one inflation balloon.

46 Claims, 8 Drawing Sheets

ANTI-OCCLUSION CATHETER

CROSS-REFERENCE TO RELATED APPLICATION

This application claims the benefit of U.S. Patent Application No. 60/219,041, titled "Carotid Filter Device," filed Jul. 18, 2000; the contents of which are incorporated by reference herein in their entirety.

BACKGROUND

Catheters, such as central venous catheters, are used for a variety of diagnostic and therapeutic purposes, including the administration of fluid and pharmaceutical agents, and for hemodialysis in patients with renal failure. Unfortunately, central venous catheters lumens are prone to occlusion due to thrombosis from retrograde blood flow. In some cases, the thrombosis can be cleared from the catheter. In other cases, the catheter must be removed and a new catheter placed. Each new catheter placement is associated with a risk of complications, including infection, hemorrhage, pneumothorax and embolus.

Some central venous catheters have a unidirectional valve at the distal catheter tip to prevent retrograde blood flow. However, catheters with such valves still occlude due to thrombosis from retrograde blood flow and the valves tend to disadvantageously impede antegrade fluid flow.

Therefore, it would be useful to have a catheter that was less prone to thrombosis from retrograde blood flow. Additionally, it would be useful to have a method of delivering fluid and pharmaceutical agents, or for performing hemodialysis, that is associated where a lower incidence of catheter replacement due to thrombosis of the catheter from retrograde blood flow.

SUMMARY

According to one embodiment of the present invention, there is provided a catheter for the administration of fluid or pharmaceutical agents, or for hemodialysis. The catheter comprises a proximal control end comprising a housing with a proximal end and a distal end; a distal delivery end; an elongated intermediate portion between the proximal control end and a distal delivery end; one or more than one delivery lumen within the intermediate portion extending from the proximal control end to the distal delivery end; one or more than one inflation balloon in each delivery lumen; and one or more than one inflation lumen in the intermediate portion extending from the proximal control end to the one or more than one inflation balloon in the one or more than one delivery lumen, and connected to the one or more than one inflation balloon through one or more than one fenestration. The proximal control end further comprises a mechanism for aspiration and injection of fluids through the distal delivery end, and the proximal control end further comprises a mechanism for controlling inflation of the one or more than one inflation balloon.

In a preferred embodiment, the one or more than one delivery lumen is two delivery lumens. In another preferred embodiment, the intermediate portion comprises an external surface and the one or more than one delivery lumen comprises an intraluminal surface, and the external surface or the intraluminal surface or both comprise at least one hydrophilic coating or comprise heparin molecules bound to the external surface or to the intraluminal surface, or both, to reduce the accumulation of thrombus and fibrin on these surfaces. In another preferred embodiment, the housing comprises one or more than one anchoring device.

In another preferred embodiment, the mechanism for aspiration and injection of fluids comprises one or more than one combined aspiration and injection port. In a particularly preferred embodiment, the combined aspiration and injection port is concave toward the distal end of the housing.

In another preferred embodiment, the one or more than one combined aspiration and injection port has a distal end and where the mechanism for aspiration and injection of fluids further comprises one or more than one aspiration and injection conduit connecting the distal end of each port to the one or more than one delivery lumen. In a particularly preferred embodiment, the mechanism for aspiration and injection of fluids further comprises constricting means for constricting the aspiration and injection conduit.

In another preferred embodiment, the mechanism for controlling inflation of the one or more than one inflation balloon comprises inflation means and deflation means. In a particularly preferred embodiment, the inflation means comprises a reservoir and an inflation actuator. The housing comprises a superior surface, and the inflation actuator can comprise a tactile recognizable surface that projects from the superior surface of the housing.

In one embodiment, the inflation means comprises an elastic bulb. In a preferred embodiment, the inflation means comprises a rigid upper unit slidably fitting into a rigid lower reservoir and separated by a reservoir spring coil within the reservoir.

In a preferred embodiment, the reservoir connects to the one or more than one inflation lumen through an antegrade flow conduit, and the inflation means further comprises a one-way, antegrade flow valve between the inflation lumen and the antegrade flow conduit. In another preferred embodiment, the reservoir connects to the one or more than one inflation lumen through one or more than one retrograde flow conduit, and where the inflation means further comprises a one-way, retrograde flow valve between the one or more than one inflation lumen and each retrograde flow conduit.

In another embodiment of the present invention, there is provided a diagnostic or therapeutic procedure in a human or animal. The method comprises the steps of providing a catheter according to the present invention, placing the catheter subcutaneously into the human or animal with the distal end inserted into a target vessel, injecting fluid into or aspirating fluid from the proximal control end of the catheter, and allowing the fluid to flow through the distal delivery end. The method can further comprise anchoring the catheter to subcutaneous tissues of the human or animal. The method can also comprise preventing flow through the distal delivery end by inflating the one or more than one inflation balloon in the distal delivery end. Inflating the one or more than one inflation balloon in the distal delivery end can be achieved by depressing a portion of the proximal control end through skin overlying the placed catheter.

The method can further comprise allowing flow through the distal delivery end to resume by deflating the one or more than one inflation balloon in the distal delivery end. Deflating the one or more than one inflation balloon in the distal delivery end is achieved by depressing a portion of the proximal control end through skin overlying the placed catheter.

FIGURES

These and other features, aspects and advantages of the present invention will become better understood with regard to the following description, appended claims, and accompanying figures where:

DESCRIPTION

In one embodiment, the present invention is a catheter suitable for a variety of diagnostic and therapeutic procedures, including the administration of fluid and pharmaceutical agents, and for hemodialysis in patients with renal failure, and suitable for implantation into a human or animal. In another embodiment, the present invention is a method of performing a diagnostic and therapeutic procedure in a human or animal, comprising providing a catheter according to the present invention. These inventions will now be discussed in detail.

Figure 1:
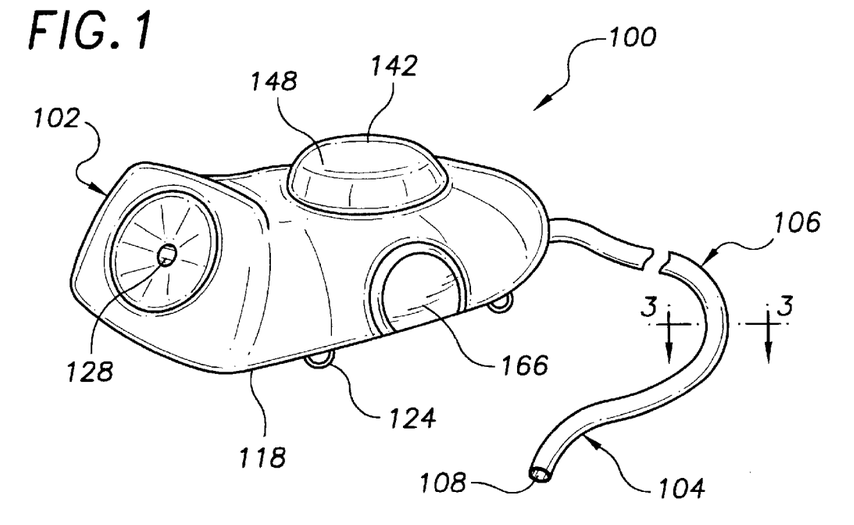
FIG. 1 is a lateral perspective view of a catheter according to one embodiment of the present invention.
Figure 2:
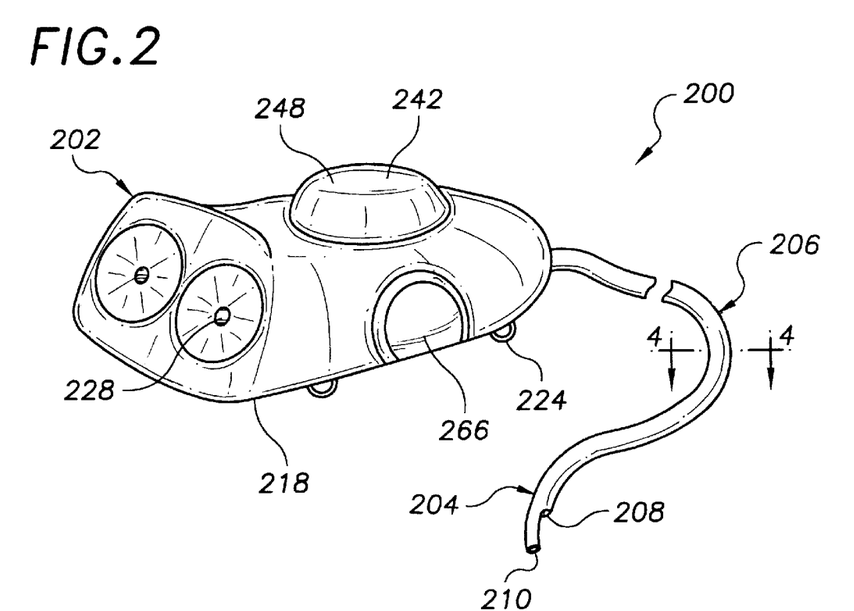
FIG. 2 is a lateral perspective view of another catheter according to another embodiment of the present invention.
Figure 3:
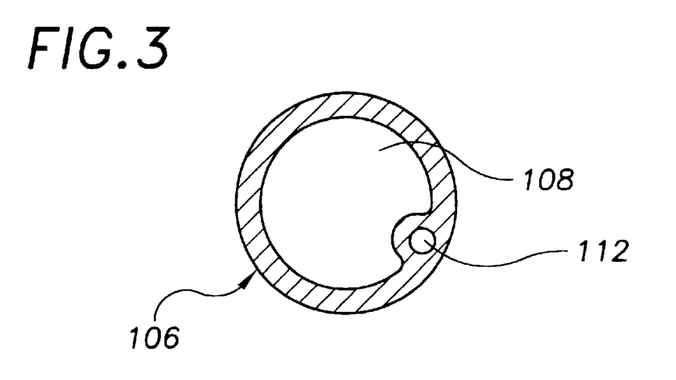
FIG. 3 is a cross-sectional view of the intermediate portion of a catheter shown in FIG. 1 having one delivery lumen taken along 3—3.
Figure 4:
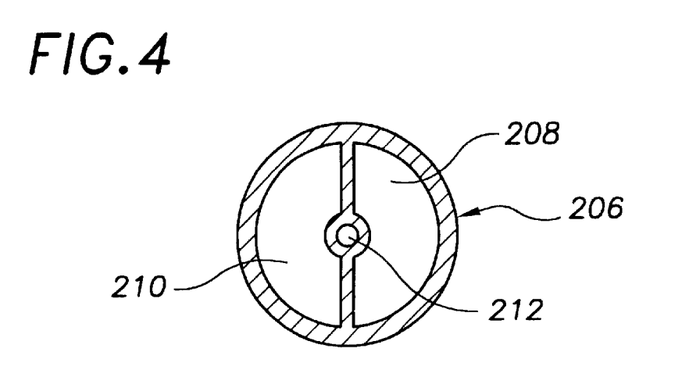
FIG. 4 is a cross-sectional view of the intermediate portion of a catheter shown in FIG. 2 having two delivery lumens taken along 4—4.

Referring now to FIG. 1 and FIG. 2, there are shown lateral perspective views of two catheters 100 and 200 according to the present invention. As can be seen, each catheter 100 and 200 generally comprises a proximal control end 102 and 202, a distal delivery end 104 and 204, and an elongated intermediate portion 106 and 206 between the proximal control end 102 and 202 and the distal delivery end 104 and 204. Each catheter also comprises one or more than one delivery lumen 108 and 208 within the intermediate portion 106 and 206. Referring now to FIG. 3 and FIG. 4, there are shown cross-sectional views of the intermediate portion 106 and 206 of the catheters shown in FIG. 1 taken along 3—3 having one delivery lumen 108, and shown in FIG. 2 taken along 4—4 having two delivery lumens 208, respectively. Each delivery lumen 108 and 208 extends generally from the proximal control end 102 and 202 to the distal delivery end 104 and 204, respectively.

In a preferred embodiment, as shown in FIG. 1, the catheter 100 has an intermediate portion 106 comprising one delivery lumen 108 and the intermediate portion 106 has an outer diameter of about 8 Fr. (2.7 mm) to about 10 Fr. (3.3 mm). This catheter 100 is suitable for the administration of fluid or pharmaceutical agents to a human or animal.

In another preferred embodiment, as shown in FIG. 2, the catheter 200 has an intermediate portion 206 comprising two delivery lumens 208 and 210 and the intermediate portion 206 has an outer diameter of about 14 Fr. (4.7 mm) to about 15 Fr. (5.0 mm). This catheter 200 is suitable for the administration of fluid or pharmaceutical agents to a human or animal, or for performing hemodialysis in patients with renal failure.

The proximal to distal length of intermediate portion 106 and 206 depends upon the intended use of the catheter 100 and 200 having the intermediate portion 106 and 206. Generally, the proximal to distal length of the intermediate portion 106 and 206 is between about 10 cm and about 50 cm. In a particularly preferred embodiment, the proximal to distal length of the intermediate portion is between about 20 cm and about 50 cm.

The cross-sectional area of intermediate portion 106 and 206 also depends upon the intended use of the catheter 100 and 200 having the intermediate portion. Generally, the radius of intermediate portion 106 is between about 1 mm and about 1.7 mm for the embodiment shown in FIG. 1, 100, and the radius of intermediate portion 206 is between about 2 mm and about 2.5 mm for the embodiment shown in FIG. 2, 200.

The intermediate portion 106 and 206 can comprise any biocompatible material suitable for implantation as will be understood by those with skill in the art with reference to this disclosure. In a preferred embodiment, the intermediate portion 106 and 206 comprises a biocompatible, braided, kink-resistant polyurethane. In a particularly preferred embodiment, the intermediate portion 106 and 206 further comprises at least one hydrophilic coating on the external surface or on each intraluminal surface, or both, to reduce the accumulation of materials leading to occlusion of the lumen, such as thrombus and fibrin. In another particularly preferred embodiment, the intermediate portion 106 and 206 comprises heparin molecules bound to the external surface or to each intraluminal surface, or both, to reduce the accumulation of thrombus and fibrin on these surfaces.

Figure 5:
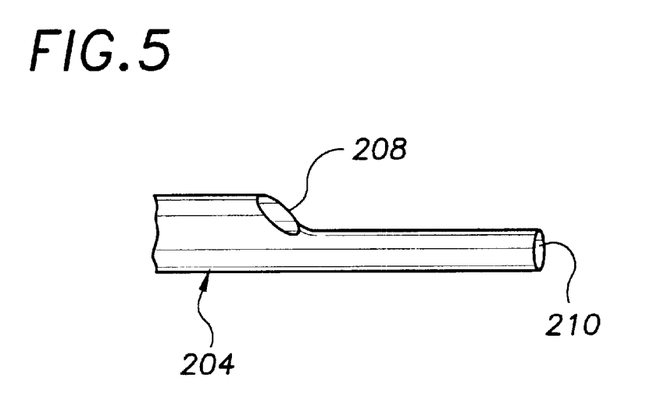
FIG. 5 is a lateral perspective view of the distal portion of a catheter shown in FIG. 2.

Referring now to FIG. 5, there is shown a lateral perspective view of the distal delivery end 204 of a catheter 200 shown in FIG. 2. As can be seen in FIG. 4 and FIG. 5, the intermediate portion 206 of the catheter 200 comprises two lumens, a first lumen 208 and a second lumen 210, and the first lumen 208 ends proximally to the second lumen 210 at the distal delivery end 204 of the catheter 200. In a preferred embodiment, the first lumen 208 ends between about 3 cm and about 4 cm proximally to the second lumen 210 at the distal delivery end 204 of the catheter 200. As will be understood by those with skill in the art with reference to this disclosure, this embodiment is particularly suitable for use in performing hemodialysis in patients with renal failure, because the first lumen can be used to aspirate venous blood during hemodialysis and the second lumen can be used to return dialyzed blood, decreasing the admixture of undialyzed and dialyzed blood and, thereby, increasing dialysis efficiency.

As can be further seen in FIG. 3 and FIG. 4, each catheter 100 and 200 of the present invention further includes at least one inflation lumen 112 and 212 extending generally from the proximal control end 102 and 202 to the distal delivery end 104 and 204. The inflation lumen can be placed within the wall of the intermediate portion 106 and 206 of the catheter 100 and 200 as shown in FIG. 3, or can be placed within the wall separating two lumens 208 and 210 as shown in FIG. 4, when more than one delivery lumen is present. The inflation lumen 112 and 212 has a sufficient cross-sectional area throughout its length to serve as a conduit for gas or fluid, such as sterile saline, sterile water or sterile contrast material, to flow from the proximal control end of the catheter to one or more than one inflation balloon at the distal delivery end of the catheter. In another preferred embodiment, the inflation lumen 112 and 212 is round in cross-section and has an internal diameter of between about 0.4 mm to about 0.7 mm. In a particularly preferred embodiment, the inflation lumen 112 and 212 is round in cross-section and has an internal diameter of about 0.55 mm.

Figure 6:
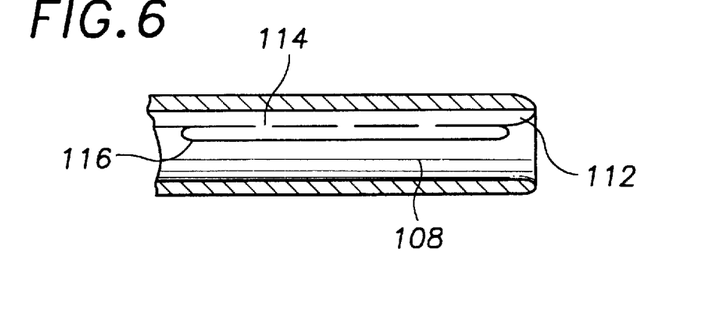
FIG. 6 is a cross-sectional view of the distal delivery end of a catheter shown in FIG. 1 having one delivery lumen, with the single inflation balloon uninflated.
Figure 7:
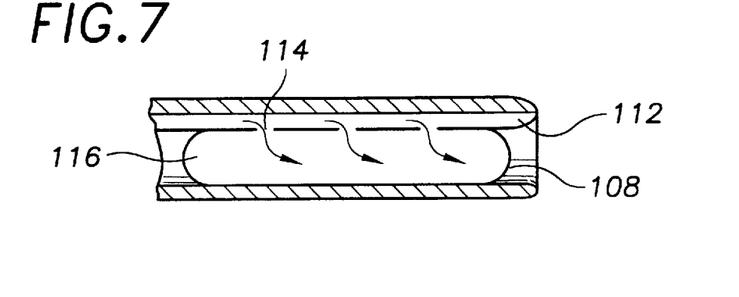
FIG. 7 is a cross-sectional view of the distal delivery end of a catheter shown in FIG. 1 having one delivery lumen, with the single inflation balloon inflated.
Figure 8:
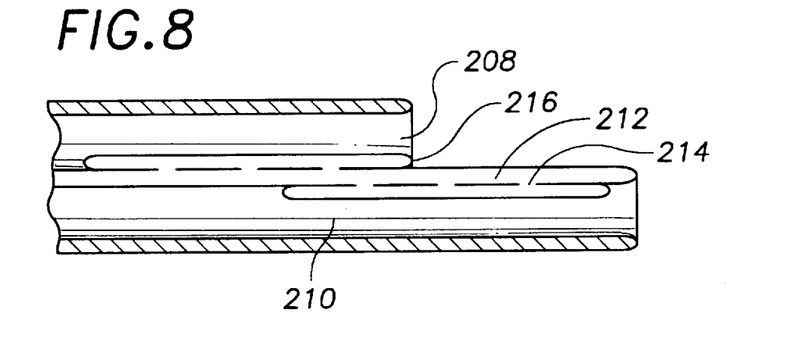
FIG. 8 is a cross-sectional view of the distal delivery end of a catheter shown in FIG. 2 having two delivery lumens, with both inflation balloons uninflated.
Figure 9:
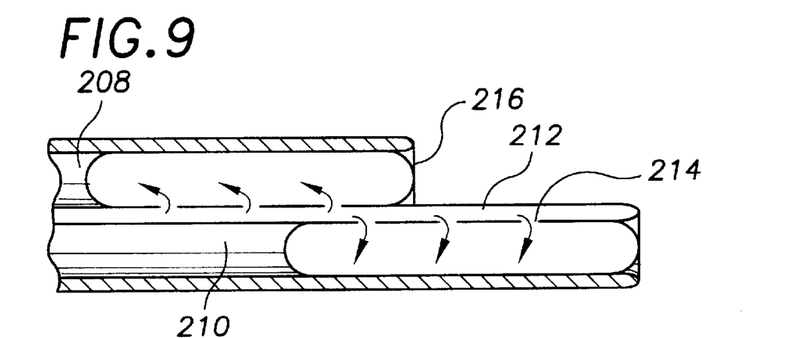
FIG. 9 is a cross-sectional view of the distal delivery end of a catheter shown in FIG. 2 having two delivery lumens, with both inflation balloons inflated.

Referring now to FIG. 6 and FIG. 7, there are shown cross-sectional views of the distal delivery end 104 of the catheter shown in FIG. 1. Referring now to FIG. 8 and FIG. 9, there are shown cross-sectional views of the distal delivery end 204 of the catheter shown in FIG. 2. As can be seen, each inflation lumen 112 and 212 ends in the distal delivery end 104 and 204 at one or more than one fenestration 114 and 214 interconnecting the inflation lumen 112 and 212 with one or more than one inflation balloon 116 and 216. In a preferred embodiment, the one or more than one fenestration 114 and 214 is present in about the distal 3 cm of the distal end of the inflation lumen 112 and 212.

Each inflation balloon 116 and 216 is preferably made of biocompatible, low pressure and high compliance latex, C-Flex, silicone rubber or other suitable material as will be understood by those with skill in the art with reference to this disclosure. Techniques for producing inflation balloons suitable to the present invention are well known to those with skill in the art. Briefly, a thin layer of balloon material is bonded around the one or more than one fenestration 114 and 214 in the delivery lumen 108 and 208, 210 at distal delivery end 104 and 204 of the catheter 100 and 200, leaving a small linear section of the material directly over the one or more than one fenestration 114 and 214 unbonded.

As shown in FIG. 6 and FIG. 8, each inflation balloon 116 and 216 is configured to have a minimum profile when deflated such that it does not significantly impede flow through the delivery lumen. As shown in FIG. 7 and FIG. 9, each inflation balloon 116 and 216 is configured to have a profile sufficient to occlude the delivery lumen at the distal delivery end of the catheter when inflated. Inflation of the inflation balloon 116 and 216, with its resultant occlusion of the delivery lumen 108 and 208, 210, prevents back flow of blood into the delivery lumen 108 and 208, 210. As can be seen in the preferred embodiment shown in FIG. 8 and FIG. 9, a single inflation lumen 212 is used to simultaneously inflate the inflation balloons 216 present in each delivery lumen 208 and 210 at the distal delivery end 204 when more than one delivery lumen is present in the catheter. However, the present invention also includes providing more than one inflation lumen 212 to inflate more than one inflation balloon 216, not shown, such that each inflation balloon 216 can be inflated independently.

Figure 10:
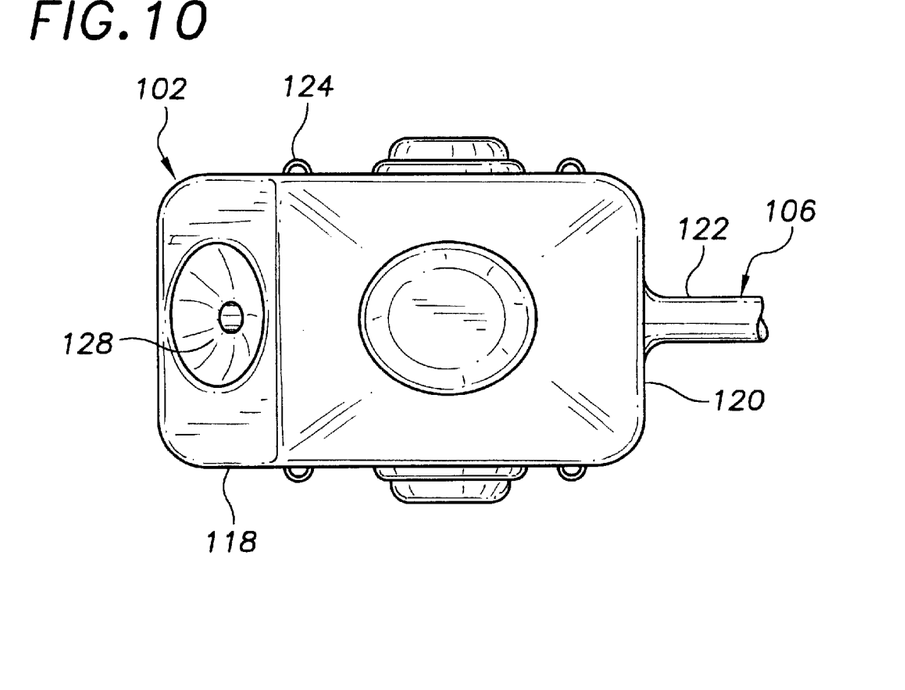
FIG. 10 is a top perspective view of the proximal control end of the catheter shown in FIG. 1.
Figure 11:
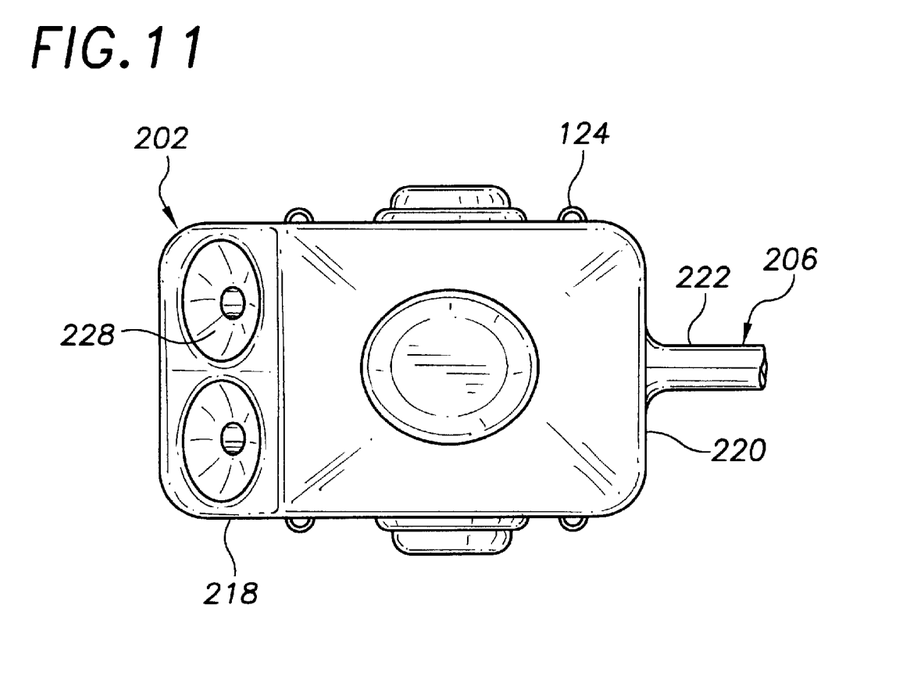
FIG. 11 is a top perspective view of the proximal control end of the catheter shown in FIG. 2.

Referring now to FIG. 10 and FIG. 11, there are shown a top perspective view of the proximal control end 102 of the catheter 100 shown in FIG. 1 and a top perspective view of the proximal control end 202 of the catheter 200 shown in FIG. 2, respectively. As can be seen in FIG. 1, FIG. 2, FIG. 10 and FIG. 11, the proximal control end 102 and 202 comprises a housing 118 and 218 with a distal end 120 and 220 connected to the proximal end of the intermediate portion 122 and 222.

The housing 118 and 218 can comprise any biocompatible material suitable for implantation as will be understood by those with skill in the art with reference to this disclosure. In a preferred embodiment, the outer casing of the housing 118 and 218 comprises titanium. Further, as will be understood by those with skill in the art with reference to this disclosure, the housing 118 and 218 has a size suitable for the intended use. By way of example, the housing 118 and 218 can be approximately 2 cm in height, 4 cm in width and 6 cm in proximal to distal length.

The housing 118 and 218 is configured to be inserted subcutaneously in a human or animal into a pouch created by blunt dissection or by the action of a high-pressure balloon dilatation instrument, according to techniques known to those with skill in the art. In a preferred embodiment, the housing 118 and 218 is configured to be anchored to the tissues forming the pouch by attaching one or more than one anchoring device 124 and 224 to the tissue forming the pouch. In a preferred embodiment, the one or more than one anchoring device 124 and 224 is a plurality of anchoring devices. In a particularly preferred embodiment, the anchoring device 124 and 224 is a semi-circular metal ring attached to the lower portion of the housing 118 and 218, and nonresorbable sutures or surgical stapes are used to attach the one more than one anchoring device 124 and 224 to the tissue forming the pouch according to techniques known to those with skill in the art.

Figure 12:
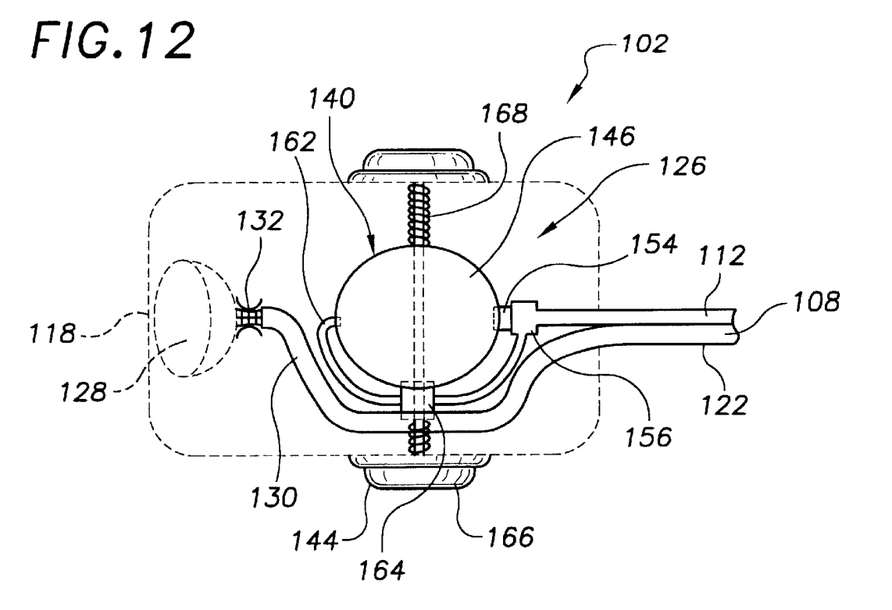
FIG. 12 is a cutaway top perspective view of the housing as shown in FIG. 1.
Figure 13:
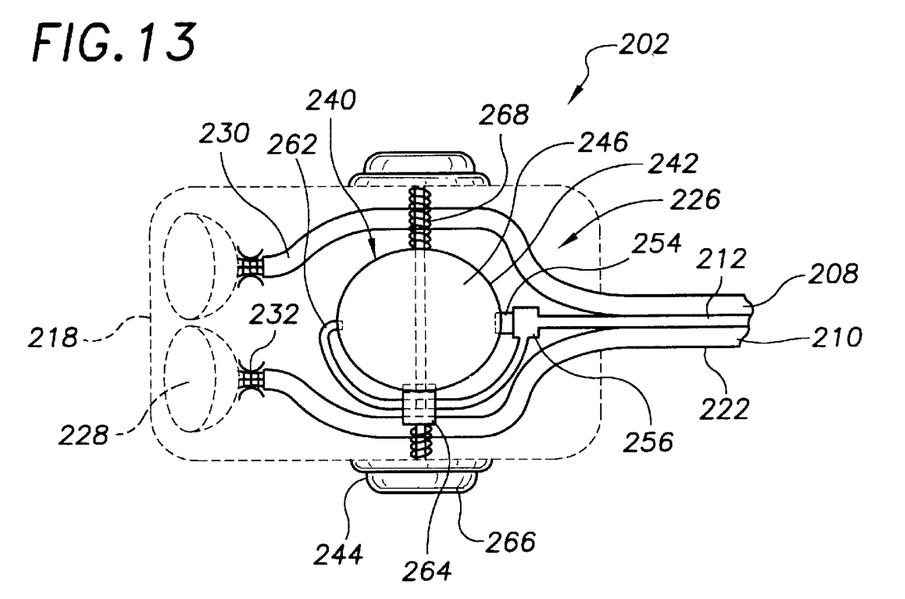
FIG. 13 is a cutaway top perspective view of the housing as shown in FIG. 2.

The housing 118 and 218 further comprises a mechanism for aspiration and injection of fluids 126 and 226 through the one or more than one delivery lumen 108 and 208, 210 of the intermediate portion 106 and 206 of the catheter 100 and 200. Referring now to FIG. 12 and FIG. 13, there are shown a cutaway top perspective view of the housing 118 and 218 as shown in FIG. 1 and FIG. 10, and in FIG. 2 and FIG. 11, respectively. As can be seen, the mechanism for aspiration and injection of fluids 126 and 226 comprises one combined aspiration and injection port 128 for the embodiment shown in FIG. 12, and two combined aspiration and injection ports 228 for the embodiment shown in FIG. 13, at the proximal end of the housing 118 and 218. In a preferred embodiment, as shown, each port 128 and 228 is configured to be concave toward the distal end of the housing 118 and 218. This configuration advantageously assists in guiding a needle used to aspirate or inject into the port 128 and 228.

The mechanism for aspiration and injection of fluids 126 and 226 further comprises an aspiration and injection conduit 130 and 230 connecting the distal end of each port 128 and 228 to the proximal end of the delivery lumen 108 and 208, 210 of the intermediate portion 106 and 206 of the catheter 100 and 200. In a preferred embodiment, the mechanism for aspiration and injection of fluids 126 and 226 further comprises constricting means 132 and 232 for constricting the proximal end of the aspiration and injection conduit 130 and 230 so as to create a water-tight seal between the port 128 and 228 and the proximal end of the delivery lumen 108 and 208, 210. In a preferred embodiment, the constricting means 132 and 232 for constricting comprises a puncture resistant, fabric sleeve surrounding the aspiration and injection conduit 130 and 230 and attached to a plurality of elastic bands that compress the sleeve radially. In a particularly preferred embodiment, the sleeve comprises poly-paraphenylene terephthalamide fibers, such as those sold under the name KEVLAR® by DuPont, with an inner rubberized surface. In another particularly preferred embodiment, the elastic bands comprise a plurality of axially oriented thin metal strips that are concave toward the center of the sleeve. The thin metal bands provide tension against the center of the sleeve radially and, thereby, the aspiration and injection conduit 130 and 230 radially, thus creating the water-tight seal in the aspiration and injection conduit 130 and 230. Other means are also suitable as will be understood by those with skill in the art with reference to this disclosure.

The constricting means 132 and 232 is used by inserting an access needle, such as a 14 or 15 gauge needle, into the port 128 and 228. The concave surface of the port 128 and 228 assists in guiding the needle into the aspiration and injection conduit 130 and 230.

Figure 14:
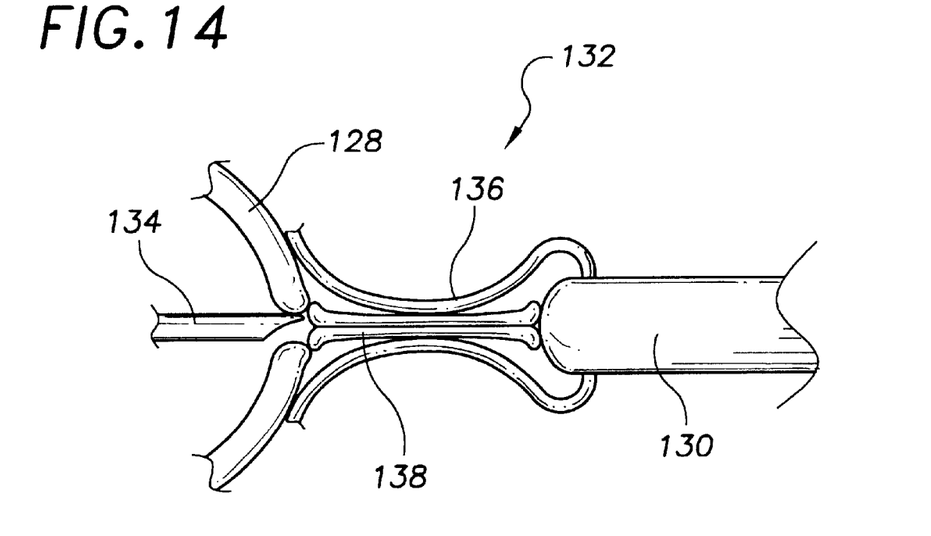
FIG. 14 and FIG. 15 are sequential close-up, cutaway, partial views of the port and means for constricting of a catheter according to the present invention in use.
Figure 15:
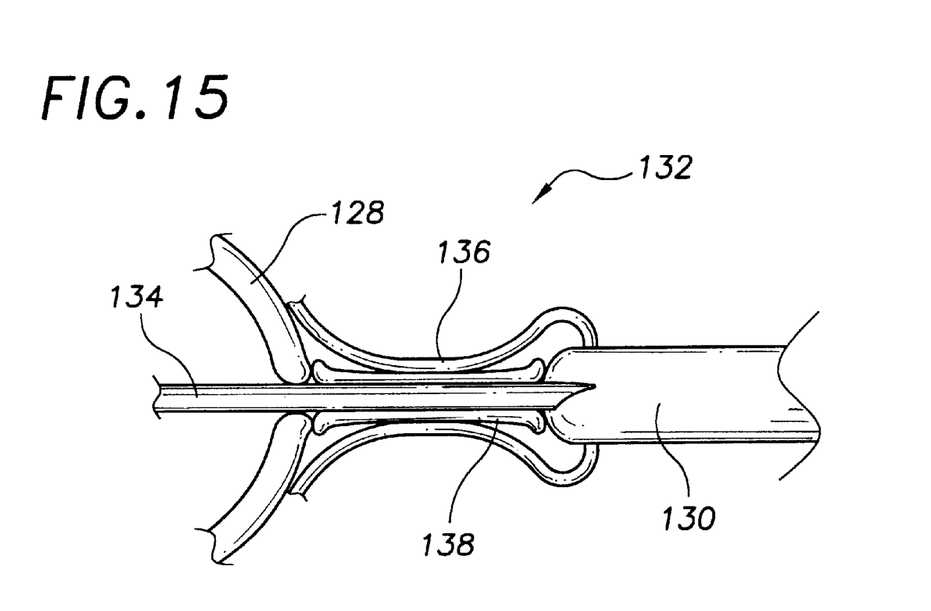

Referring now to FIG. 14 and FIG. 15, there are shown close-up, cutaway, partial views of the port 128 and one embodiment of the constricting means 132 while in use. The constricting means 232 can be configured in a corresponding manner to the constricting means 132. As can be seen in these Figures, as the needle 134 enters the port 128 and constricting means 132, it separates elastic bands 136 and opens a passage into the conduit 130. A sleeve 138 assists in preventing perforation of the conduit 130 by the tip of the needle 134. Withdrawal of the needle 134 allow the tension provided by the elastic bands 136 to again seal the conduit.

The housing 118 and 218 further comprises a mechanism for controlling inflation 140 and 240 of the one or more than one inflation balloon 116 and 216. The mechanism 140 and 240 comprises an inflation means 142 and 242 and comprises a deflation means 144 and 244. Though the inflation means 142 and 242 and deflation means 144 and 244 are disclosed with reference to particular preferred embodiments, it will be understood by those with skill in the art with reference to this disclosure that other embodiments are possible and are within the contemplated scope of this invention.

Figure 16:
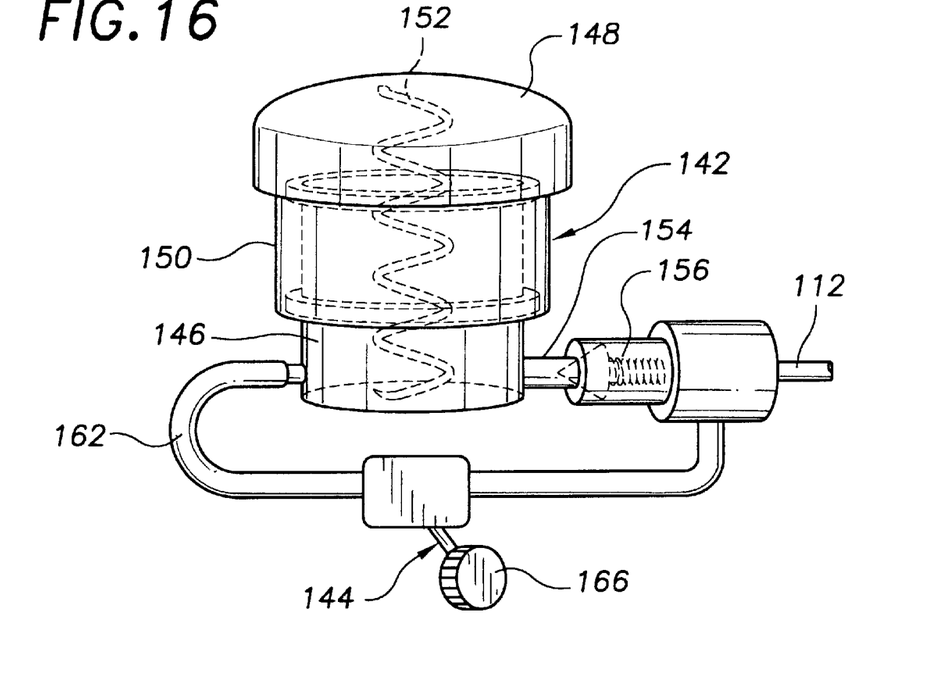
FIG. 16 is a partial side perspective view of the inflation means and the deflation means of a catheter according to the present invention.
Figure 17:
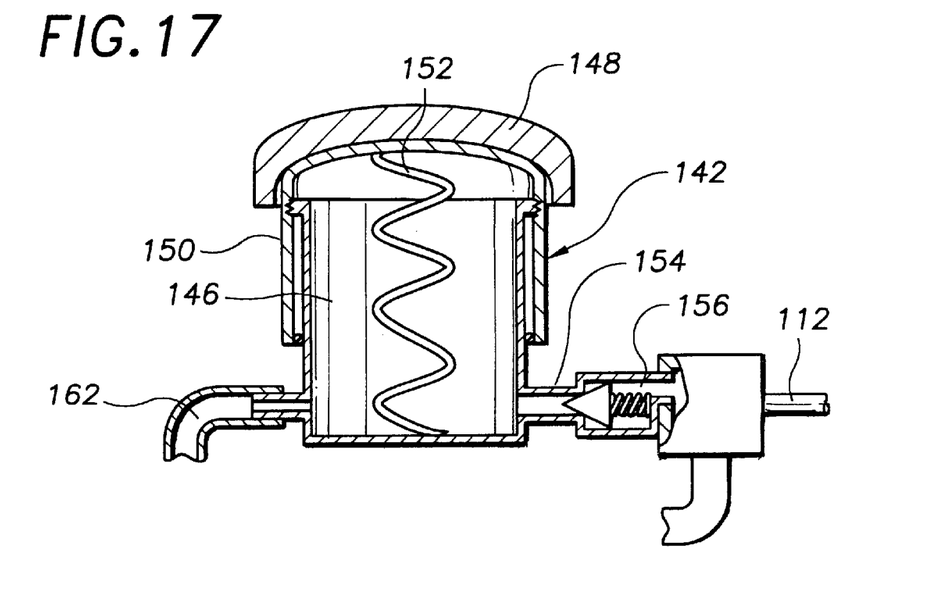
FIG. 17 is a partial cutaway, side perspective view of the inflation means and the deflation means according to the present invention.

Referring again to FIG. 1, FIG. 2, FIG. 12 and FIG. 13, and referring now to FIG. 16 and FIG. 17, there are shown in FIG. 16 and FIG. 17, respectively, a partial side perspective view of the inflation means 142 and the deflation means 144 and a partial cutaway, side perspective view of the inflation means 142 and the deflation means 144 of the catheter 100 shown in FIG. 1. The inflation means 242 and the deflation means 244 of the catheter 200 can be configured in a corresponding manner to the inflation means 142 and the deflation means 144 of the catheter 100. As can be seen, the inflation means 142 and 242 comprises a reservoir 146 and 246 and an inflation actuator 148 and 248. As shown in the Figures, the inflation actuator 148 and 248 preferably comprises a tactile recognizable surface that projects from the superior surface of the housing 118 and 218 and is passively maintained in the balloon deflated position. The inflation means 142 and 242 can comprise an elastic bulb, as shown in FIG. 1, FIG. 2, FIG. 12 and FIG. 13, where part of the bulb serves as the reservoir 146 and 246 and part serves as the inflation actuator 148 and 248 and projects from the superior surface of the housing 118 and 218. Alternately, as shown in FIG. 16 and FIG. 17, the inflation means 142 can comprise a collapsible unit such as a rigid upper unit 150 slidably fitting into a rigid lower reservoir 146 and held apart in the balloon deflated position by a reservoir spring coil 152 within the reservoir 146. Other inflation means are also suitable, as will be understood by those with skill in the art with reference to this disclosure.

Figure 18:
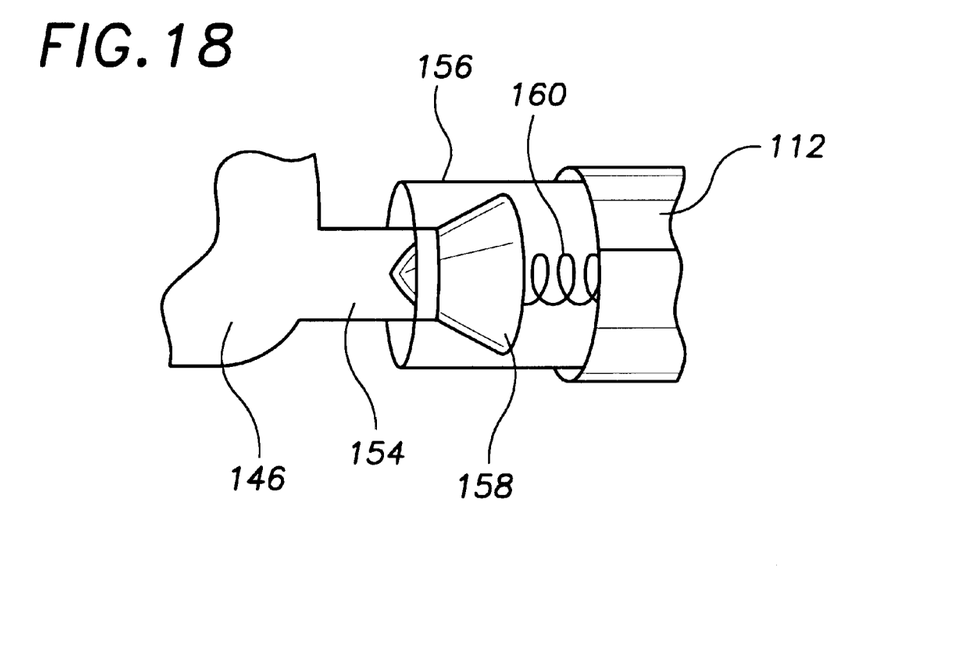
FIG. 18 is a top perspective, cutaway view of a one-way, antegrade flow valve according to the present invention in the inflation balloon deflated position.

At the distal end, the reservoir 146 and 246 connects to an antegrade flow conduit 154 and 254 and, thereby, to the proximal end of the inflation lumen 112 and 212. The antegrade flow conduit 154 is interrupted by a one-way, antegrade flow valve 156. Referring now to FIG. 18, there is shown a top perspective, cutaway view of a one-way, antegrade flow valve 156 according to the present invention. The one-way, antegrade flow valve 156 comprises a antegrade flow conduit sealer 158 generally held in the inflation balloon deflated position by a antegrade valve spring coil 160 as shown.

Figure 19:
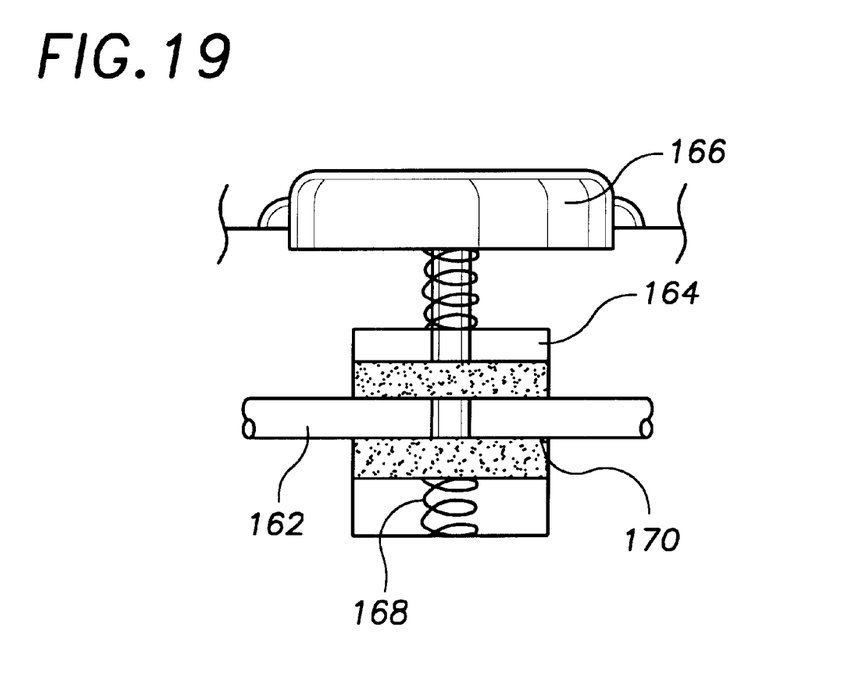
FIG. 19 is a top perspective, cutaway view of a one-way, retrograde flow valve according to the present invention in the inflation balloon inflated position.

At the proximal end, the reservoir 146 and 246 connects to one or more than one retrograde flow conduit 162 and 262 and, thereby from each retrograde flow conduit 162 and 262, to the proximal end of the inflation lumen 112 and 212. Each retrograde flow conduit 162 and 262 is interrupted by a one-way, retrograde flow valve 164 and 264. Each one-way, retrograde flow valve 164 and 264 is connected to a deflation actuator 166 and 266. Each deflation actuator 166 and 266 preferably comprises a tactile recognizable surface that projects from the lateral surface of the housing 118 and 218 and is passively maintained in that balloon inflated position by a retrograde valve spring coil 168 and 268 within the retrograde flow valve 164 and 264. Referring now to FIG. 19, there is shown a top perspective, cutaway view of a one-way, retrograde flow valve 164 according to the present invention. The one-way, retrograde flow valve 264 of the catheter 200 can be configured in a corresponding manner to the one-way, retrograde flow valve 164 of the catheter 100. As can be seen, the one-way, retrograde flow valve 164 comprises a retrograde flow conduit 162 and retrograde flow conduit sealer 170 generally held in the inflation balloon inflated position by a retrograde valve spring coil 168.

The present invention further comprises a method of performing a diagnostic and therapeutic procedure in a human or animal. The method comprises providing a catheter according to the present invention. The catheter is then placed subcutaneously into the human or animal using standard techniques with the distal end inserted intravenously and advanced into the appropriate position for performing the diagnostic or therapeutic procedure. Briefly, under sterile conditions and, preferably, local anesthesia, an entry needle is used to percutaneously puncture the target vessel. Next, a guidewire is coaxially inserted into the target vessel and the entry needle is withdrawn over the guidewire while maintaining access to the target vessel.

Then, the subcutaneous tissues adjacent the entry site are incised and a subcutaneous pouch is created sufficient to hold the proximal control end of a catheter according to the present invention using a tunneling device. The tunneling device is then used to advance the catheter through the subcutaneous pouch and advance the distal end of the catheter exteriorly through the incision at the guidewire entry site. The housing is preferably secured within the pouch as disclosed above, and the entry incision used to create the pouch is closed, such as by suturing.

Next, a peel-away sheath is then inserted into the target vessel over the guide wire and is advanced to the appropriate location with the target vessel, such as into the superior vena cava or the inferior vena cava. The guidewire is then removed from the sheath and the distal end of the catheter is inserted into the target vessel through the sheath. The sheath is then removed and the catheter seated into its final position subcutaneously. Finally, the entry site incision is closed and the incisions are dressed in a standard manner.

Once, the catheter is placed subcutaneously, it is used as follows. Fluid is administered or withdrawn by needle access through the port. The needle access opens the means for constricting, when present.

To stop retrograde flow through the lumen of the intermediate portion, the inflation means is actuated, such as by depression of the inflation actuator through the overlying skin. This action sends fluid from the reservoir into the antegrade flow conduit, opening the antegrade flow valve and inflating the one or more than one inflation balloon. Inflating the one or more than one inflation balloon stops retrograde flow into the one or more than one lumen in the distal end of the catheter. Fluid can be injected into the lumen through a port simultaneously to assist in stopping retrograde flow. Additionally, fluid can be injected into the lumen through a port simultaneously to confirm occlusion of the lumen by one or more than one inflation balloon using tactile feedback. Once actuation of the inflation means stops, fluid pressure distal to the antegrade flow valve closes the antegrade flow valve and prevents retrograde flow into the reservoir, thus maintaining inflation of the one or more than one inflation balloon and occlusion of the distal catheter.

When patency of the lumen of the intermediate portion is again needed, the deflation means is actuated, such as by depression of the deflation actuator through the overlying skin. This action sends fluid from the one or more than one inflation balloon into the retrograde flow conduit, opening the retrograde flow valve and into the reservoir. Once actuation of the deflation means stops, the retrograde flow valve closes preventing antegrade flow from the reservoir, thus maintaining deflation of the one or more than one inflation balloon and patency of the distal catheter.

Although the present invention has been discussed in considerable detail with reference to certain preferred embodiments, other embodiments are possible. For example, the catheter of the present invention can be used as a gastric or enteral feeding tube to prevent retrograde flow of gastric or enteral contents. Therefore, the scope of the appended claims should not be limited to the description of preferred embodiments contained in this disclosure.

I claim:

1. A method of performing a diagnostic or therapeutic procedure in a human or animal comprising the steps of:
   a) providing a catheter for the administration of fluid or pharmaceutical agents, or for hemodialysis comprising:
      i) a proximal control end comprising a housing with a proximal end and a distal end;
      ii) a distal delivery end;
      iii) an elongated intermediate portion between the proximal control end and a distal delivery end;
      iv) one or more than one delivery lumen within the intermediate portion extending from the proximal control end to the distal delivery end;
      v) one or more than one inflation balloon in each delivery lumen; and
      vi) one or more than one inflation lumen in the intermediate portion extending from the proximal control end to the one or more than one inflation balloon in the one or more than one delivery lumen, and connected to the one or more than one inflation balloon through one or more than one fenestration;
      where the proximal control end further comprises a mechanism for aspiration and injection of fluids through the distal delivery end; and
      where the proximal control end further comprises a mechanism for controlling inflation of the one or more than one inflation balloon;
   b) placing the catheter subcutaneously into the human or animal with the distal end inserted into a target vessel;
   c) injecting fluid into or aspirating fluid from the proximal control end of the catheter; and
   d) allowing the fluid to flow through the distal delivery end;
      where inflating the one or more than one inflation balloon in the distal delivery end is achieved by depressing a portion of the proximal control end through skin overlying the placed catheter.

2. The method of claim 1, where the mechanism for controlling inflation of the one or more than one inflation balloon of the provided catheter comprises inflation means and deflation means.

3. The method of claim 2, where the inflation means comprises a reservoir and an inflation actuator.

4. The method of claim 3, where the housing has a superior surface, and where the inflation actuator comprises a tactile recognizable surface that projects from the superior surface of the housing.

5. The method of claim 3, where the reservoir connects to the one or more than on inflation lumen through an antegrade flow conduit, and where the inflation means further comprises a one-way, antegrade flow valve between the inflation lumen and the antegrade flow conduit.

6. The method of claim 3, where the reservoir connects to the one or more than one inflation lumen through one or more than one retrograde flow conduit, and where the inflation means further comprises a one-way, retrograde flow valve between the one or more than one inflation lumen and each retrograde flow conduit.

7. The method of claim 2, where the inflation means comprises an elastic bulb.

8. The method of claim 2, where the inflation means comprises a rigid upper unit slidably fitting into a rigid lower reservoir and separated by a reservoir spring coil within the reservoir.

9. The method of claim 1, where the mechanism for aspiration and injection of fluids of the provided catheter comprises one or more than one combined aspiration and injection port.

10. The method of claim 9, where each of the one or more than one combined aspiration and injection port has a distal end and where the mechanism for aspiration and injection of fluids further comprises one or more than one aspiration and injection conduit connecting the distal end of each port to the one or more than one delivery lumen.

11. The method of claim 10, where the mechanism for aspiration and injection of fluids further comprises constricting means for constricting the aspiration and injection conduit.

12. The method of claim 9, where the combined aspiration and injection port is concave toward the distal end of the housing.

13. The method of claim 1, further comprising preventing flow through the distal delivery end by inflating the one or more than one inflation balloon in the distal delivery end.

14. The method of claim 13, further comprising allowing flow through the distal delivery end to resume by deflating the one or more than one inflation balloon in the distal delivery end.

15. The method of claim 14, where deflating the one or more than one inflation balloon in the distal delivery end is achieved by depressing a portion of the proximal control end through skin overlying the placed catheter.

16. The method of claim 1, further comprising anchoring the catheter to subcutaneous tissues of the human or animal.

17. The method of claim 1, where the one or more than one delivery lumen of the provided catheter is two delivery lumens.

18. The method of claim 1, where the one or more than one delivery lumen of the provided catheter has an axial length of between about 10 cm and about 50 cm.

19. The method of claim 1, where the intermediate portion of the provided catheter has a cross-sectional area and where the cross-sectional area is between about 1 cm and about 3 cm.

20. The method of claim 1, where the intermediate portion of the provided catheter comprises an external surface and the one or more than one delivery lumen comprises an intraluminal surface; and
where the external surface or the intraluminal surface or both comprise at least one hydrophilic coating.

21. The method of claim 1, where the intermediate portion of the provided catheter comprises an external surface and the one or more than one delivery lumen comprises an intraluminal surface; and
where the external surface or the intraluminal surface or both comprise heparin molecules bound to the external surface or to the intraluminal surface, or both, to reduce the accumulation of thrombus and fibrin on these surfaces.

22. The method of claim 1, where the inflation lumen of the provided catheter has an internal diameter of between about 0.4 and about 0.7 mm.

23. The method of claim 1, where the housing of the provided catheter comprises one or more than one anchoring device.

24. A method of performing a diagnostic or therapeutic procedure in a human or animal comprising the steps of:
a) providing a catheter for the administration of fluid or pharmaceutical agents, or for hemodialysis comprising:
i) a proximal control end comprising a housing with a proximal end and a distal end;
ii) a distal delivery end;
iii) an elongated intermediate portion between the proximal control end and a distal delivery end;
iv) one or more than one delivery lumen within the intermediate portion extending from the proximal control end to the distal delivery end;
v) one or more than one inflation balloon in each delivery lumen; and
vi) one or more than one inflation lumen in the intermediate portion extending from the proximal control end to the one or more than one inflation balloon in the one or more than one delivery lumen, and connected to the one or more than one inflation balloon through one or more than one fenestration;
where the proximal control end further comprises a mechanism for aspiration and injection of fluids through the distal delivery end; and
where the proximal control end further comprises a mechanism for controlling inflation of the one or more than one inflation balloon;
where deflating the one or more than one inflation balloon in the distal delivery end is achieved by depressing a portion of the proximal control end through skin overlying the placed catheter;
b) placing the catheter subcutaneously into the human or animal with the distal end inserted into a target vessel;
c) injecting fluid into or aspirating fluid from the proximal control end of the catheter; and
d) allowing the fluid to flow through the distal delivery end;
where deflating the one or more than one inflation balloon in the distal delivery end is achieved by depressing a portion of the proximal control end through skin overlying the placed catheter.

25. The method of claim 24, where the mechanism for controlling inflation of the one or more than one inflation balloon of the provided catheter comprises inflation means and deflation means.

26. The method of claim 25, where the inflation means comprises a reservoir and an inflation actuator.

27. The method of claim 26, where the housing has a superior surface, and where the inflation actuator comprises a tactile recognizable surface that projects from the superior surface of the housing.

28. The method of claim 26, where the reservoir connects to the one or more than one inflation lumen through an antegrade flow conduit, and where the inflation means further comprises a one-way, antegrade flow valve between the inflation lumen and the antegrade flow conduit.

29. The method of claim 26, where the reservoir connects to the one or more than one inflation lumen through one or more than one retrograde flow conduit, and where the inflation means further comprises a one-way, retrograde flow valve between the one or more than one inflation lumen and each retrograde flow conduit.

30. The method of claim 25, where the inflation means comprises an elastic bulb.

31. The method of claim 25, where the inflation means comprises a rigid upper unit slidably fitting into a rigid lower reservoir and separated by a reservoir spring coil within the reservoir.

32. The method of claim 24, where the mechanism for aspiration and injection of fluids of the provided catheter comprises one or more than one combined aspiration and injection port.

33. The method of claim 32, where each of the one or more than one combined aspiration and injection port has a distal end and where the mechanism for aspiration and injection of fluids further comprises one or more than one aspiration and injection conduit connecting the distal end of each port to the one or more than one delivery lumen.

34. The method comprising 33, where the mechanism for aspiration and injection of fluids further comprises constricting means for constricting the aspiration and injection conduit.

35. The method of claim 32, where the combined aspiration and injection port is concave toward the distal end of the housing.

36. The method of claim 21, further comprising preventing flow through the distal delivery end by inflating the one or more than one inflation balloon in the distal delivery end.

37. The method of claim 36, where inflating the one or more than one inflation balloon in the distal delivery end is achieved by depressing a portion of the proximal control end through skin overlying the placed catheter.

38. The method of claim 36, further comprising allowing flow through the distal delivery end to resume by deflating the one or more than one inflation balloon in the distal delivery end.

39. The method of claim 21, further comprising anchoring the catheter to subcutaneous tissues of the human or animal.

40. The method of claim 24, where the one or more than one delivery lumen of the to provided catheter is two delivery lumens.

41. The method of claim 24, where the one or more than one delivery lumen of the provided catheter has an axial length of between about 10 cm and about 50 cm.

42. The method of claim 24, where the intermediate portion of the provided catheter has a cross-sectional area and where the cross-sectional area is between about 1 cm and about 3 cm.

43. The method of claim 24, where the intermediate portion of the provided catheter comprises an external surface and the one or more than one delivery lumen comprises an intraluminal surface; and where the external surface or the intraluminal surface or both comprise at least one hydrophilic coating.

44. The method of claim 24, where the intermediate portion of the provided catheter comprises an external surface and the one or more than one delivery lumen comprises an intraluminal surface; and where the external surface or the intraluminal surface or both comprise heparin molecules bound to the external surface or to the intraluminal surface, or both, to reduce the accumulation of thrombus and fibrin on these surfaces.

45. The method of claim 24, where the inflation lumen of the provided catheter has an internal diameter of between about 0.4 and about 0.7 mm.

46. The method of claim 24, where the housing of the provided catheter comprises one or more than one anchoring device.

* * * * *